US006235532B1

(12) United States Patent
Uttamchandani et al.

(10) Patent No.: US 6,235,532 B1
(45) Date of Patent: May 22, 2001

(54) FURFURALDEHYDE DETECTOR AND METHOD OF MANUFACTURING THE SAME

(75) Inventors: Deepak Gulabrai Uttamchandani; Robert George Blue, both of Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 09/341,155

(22) PCT Filed: Jan. 13, 1998

(86) PCT No.: PCT/GB98/00096

§ 371 Date: Jul. 22, 1999

§ 102(e) Date: Jul. 22, 1999

(87) PCT Pub. No.: WO98/32012

PCT Pub. Date: Jul. 23, 1998

(30) Foreign Application Priority Data

Jan. 15, 1997 (GB) .................................................. 9700745

(51) Int. Cl.⁷ .................................................. G01N 33/26
(52) U.S. Cl. ........................... 436/60; 436/128; 436/164; 436/166; 422/61; 422/82.05
(58) Field of Search ................................ 436/128, 56, 60, 436/164, 166, 177–178; 422/61, 82.05, 82.11

(56) References Cited

U.S. PATENT DOCUMENTS 4,514,503 * 4/1985 Orelup ..................................... 436/60
5,646,047 * 7/1997 Bird et al. ............................ 436/128

FOREIGN PATENT DOCUMENTS 27 32 288 A1   2/1979 (DE) .
93 21513      10/1993 (WO) .

OTHER PUBLICATIONS

Ingersoll Christine M, Bright Frank V; "Using sol–gel–based platforms for chemical sensors"; vol. 27, No. 1, Washington, DC, USA, p. 26–31 XPOO2060846.

Pahlavanpour B et al; "Development of a rapid spectrophotometry method for analysis of furfuraldehyde in transformer oil as an indication of paperageing"; IEEE 1993 Annual Report; pp. 493–498, XPOO2060847.

* cited by examiner

Primary Examiner—Lyle A. Alexander
(74) Attorney, Agent, or Firm—Alston & Bird LLP

(57) ABSTRACT

Sensing the presence of furfuraldehyde (FFA) in oil is effected by a porous solid sensor (10) comprising aniline acetate entrapped in an inert matrix. The matrix may be a sol-gel preferably based on methyltrimethoxysilane. The solid sensor (10) reacts with FFA to form a pink colored complex which has a characteristic which correlates with the concentration of FFA in the oil and which can be measured photo-optically. Photo-optical measurement may be by absorption or fluorescence when the sensor is irradiated with an interrogating beam. The absorption maximum wavelength is about 525 nm and irradiation at that wavelength produces a maximum fluorescent output at about 570 nm.

10 Claims, 3 Drawing Sheets

FURFURALDEHYDE DETECTOR AND METHOD OF MANUFACTURING THE SAME

The present invention relates to detection of furfuraldehyde (FFA) in transformer oil.

The lifetime of a transformer is often limited by the ageing or degradation (polymerisation) of the paper insulation which is used on the transformer windings. Indirect methods of examining the paper insulation inside a transformer have to be used because it is impractical to examine the paper insulation inside a transformer directly.

A known method of determining the quality of the paper insulation relies on the fact that the thermal ageing process of the paper is accompanied by the evolution of several paper by-products into the transformer oil in which the transformer core is immersed. These by-products include gases such as CO and $CO_2$ and a chemical compound called furfuraldehyde.

The gases CO and $CO_2$ can be produced by the thermal degradation of the oil itself. Furfuraldehyde, however, is only produced by degradation of the paper, so its detection can provide an early indication of the overheating of the paper insulation.

The current practice involves periodically collecting samples of oil from the transformer or transformers to be tested, transporting the samples to a laboratory, usually remote from the transformers, and analysing the samples using a colourimetric process.

The colourimetric process relies on the specific reaction between FFA and the compound aniline acetate which yields a complex with a bright pink colour the intensity of which is a characteristic which can be measured photo-optically and which correlates with the concentration of FFA in the transformer oil. The liquid reagents used during the chemical analysis (and the fumes produced) are toxic if ingested and therefore great care must be taken during the laboratory chemical analysis.

Present practices therefore do not enable an on-the-spot assessment (or estimate) of the state of the paper insulation via FFA measurements to be made. The analyses are conducted in a chemical laboratory, sometimes days after the oil samples were actually extracted from the transformers. Thus the analysis is slow and expensive. This procedure also introduces a long time delay (for example one week) between taking a sample of oil from a transformer containing faulty paper insulation and determining that the paper insulation is faulty. The effect of this delay is that the transformer is in use for the delay period (one week) even though the paper insulation is faulty and in need of replacement.

It is an object of the present invention to mitigate or obviate one or more of the above disadvantages.

This is achieved by entrapping aniline acetate which is indicative of the state of the paper in an inert matrix to produce a porous solid sensor which facilitates on-site detection of paper degradation without exposing the user to toxic chemicals.

According to a first aspect of the present invention there is provided a solid sensor for detecting furfuraldehyde in oil, where the sensor comprises a solidified matrix in which aniline acetate is entrapped, and where the matrix is made of an inert material which allows ingress of furfuraldehyde from the oil to react with the aniline acetate to yield an entrapped complex having a characteristic which is photo-optically measurable and which correlates with the concentration of furfuraldehyde in the oil.

Preferably, the matrix material is a sol-gel.

The sold sensor may have sufficient thickness to be self-supporting or it may take the form of a thin film or coating carried by a substrate which may be transparent (e.g. glass), or optically reflective to permit photo-optic measurement by an interrogating beam. The solid sensor and its substrate may alternatively form a waveguide structure for an interrogation beam.

According to a second aspect of the present invention there is provided a method of manufacturing a solid sensor for detecting furfuraldehyde in oil, the method comprising the steps: of forming a colloidal suspension (sol) of methyltrimethoxysilane (MTMS) in a catalyst at an elevated temperature, reducing the temperature of the sol to ambient, preparing liquid aniline acetate, where the reaction temperature is maintained below ambient (20° C.) during the preparation of the liquid aniline acetate, and thereafter stirring into the sol at ambient temperature a quantity of the prepared aniline acetate in liquid form so as to form a sol and aniline acetate mixture, and thereafter gelating and drying the mixture in air substantially at ambient temperature.

By virtue of the low temperatures used in preparing the solid sensor, and particularly the low reaction temperature during preparation of the liquid aniline acetate, the chemical functionality of the liquid aniline acetate is retained despite being encapsulated in the solid sensor.

According to a third aspect of the present invention there is provided a method of determining the status of paper insulation in an oil-filled transformer, comprising the steps of: providing a solid sensor formed of a porous solidified inert matrix in which aniline acetate is entrapped, inserting the sensor into the oil for a time sufficient to allow furfuraldehyde to react with aniline acetate encapsulated in the sensor so as to form a complex having a characteristic which is photo-optically measurable and which correlates with the concentration of furfuraldehyde in the oil, thereafter irradiating the sensor with an optical input signal of a fixed wavelength, detecting and measuring an optical output signal received from the sensor, comparing the output signal with a reference to determine the amount of furfuraldehyde that was detected, and providing a qualitative indication of the state of the paper insulation based on the amount of furfuraldehyde that was detected.

Preferably, an additional step of removing the sensor from the oil is performed prior to irradiating the sensor with the optical input signal of a fixed wavelength.

It will be understood that the method also includes the step of selecting the fixed wavelength from the range of 500 nm to 600 nm.

The characteristic which correlates with the concentration of furfuraldehyde in the oil may be the pink colour intensity of the complex, which is measurable by absorbance of the optical input signal so that the output signal is of the same wavelength as the input signal. Alternatively, the characteristic may be the fluorescence of the complex when irradiated by the optical input signal so that the output signal is of a different wavelength from the input signal.

These and other aspects of the invention will become apparent from the following description when taken in combination with the accompanying drawings in which:

BRIEF DESCRIPTION OF THE DRAWINGS

FIG. 3b shows a side view of the coated glass slide of FIG. 3a;

FIG. 5b shows a cross-sectional view of the optical fibre of FIG. 5a.

Referring to FIG. 1, which shows a circular or disc-shaped sensor 10 for detecting furfuraldehyde, the sensor is a solidified matrix made of an inert material in which aniline acetate is entrapped. The solidified matrix is a sol-gel material which allows ingress of furfuraldehyde from transformer oil to react with the aniline acetate to yield an entrapped complex with a characteristic which is photo-optically measurable and which correlates with the concentration of furfuraldehyde in the oil, for example the characteristic may be the colour which is detectable by colourimetric analysis. To produce this sensor 10, the following procedure is followed.

Figure 1:
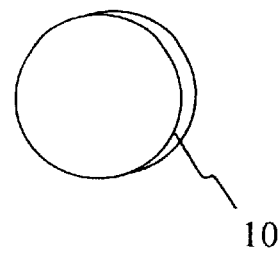
FIG. 1 shows a solid disc-shaped furfuraldehyde sensor in accordance with one embodiment of the invention.

Initially, a sol is prepared. A sol is a colloidal suspension of solid particles in a liquid. To prepare a sol to produce an FFA sensor, 28.5 ml of 98% Methyltrimethoxysilane (MTMS) (available from Aldrich) is placed in a glass jar and heated to 82° C. in an air ambient. To promote hydrolysis, a catalyst, for example 5 ml of 0.01M hydrochloric acid (HCl), is slowly mixed with the MTMS, and the solution is stirred for 5 minutes. The solution consisting of about 85% by volume MTMS and 15% by volume catalyst is placed onto a cold stirrer where it is stirred while it cools for 2 hours. This is the MTMS sol.

If 10 ml of 0.01M HCl is used instead of 5 ml of 0.01M HCl then the sol will become cloudy in approximately 5 minutes and produce discs that are more opaque and in some cases milky white in appearance. If 1.5 ml of 0.01M HCl is used instead of 5 ml of 0.01M HCl then the discs produced are cracked, broken, deformed, and in some cases more opaque. If the MTMS sol is prepared by heating the MTMS to a temperature in the range 25 to 60° C. (rather than 82° C.) then the gels that are eventually produced have a milky opaque appearance which detracts from their quality as optical devices. Raising the temperature to approximately 80° C. removes this problem of producing milky opaque gels. Raising the temperature to above 65° C. allows evaporation of methanol (which boils at 65° C.) which induces further benefits, such as reducing the risk of cracking in films. The boiling point of MTMS is 102° C., therefore an acceptable range would be between approximately 75° C. and 90° C.

To prepare aniline acetate, a glass vessel containing 90 ml of 99.8% glacial acetic acid is placed in an ice bath and allowed to cool to 15° C. Once the glacial acetic acid has cooled to 15° C., 10 ml of 99% pure aniline (available from Aldrich) is slowly mixed with the glacial acetic acid; care is taken to ensure that the reaction temperature remains below 20° C., although slightly higher temperatures may not have a detrimental effect on the aniline acetate produced.

To prepare an aniline acetate sol-gel, 4 ml of aniline acetate is mixed into the MTMS sol (4 ml added to 35.5 ml is an addition of about 12% by volume) at a temperature of 24.5° C., and stirred for 10 minutes. To prepare discs, the wells of disposable multiwell plates, (available from BDH) are cleaned with isopropyl alcohol. 0.5 ml of aniline acetate doped MTMS sol is introduced into each well on a plate. The plate is covered with a lid and left for approximately 1 month in an air ambient at between 22° C. and 25° C. to gelate and dry. After the 1 month period each well contains a disc-shaped aniline acetate doped sol-gel which is approximately 1 mm thick. The aniline acetate doped sol-gel can be used as a sensor 10 because the sol-gel is porous: it allows furfuraldehyde to permeate through the sol-gel material. Thus, sol-gel material allows ingress of furfuraldehyde. Furfuraldehyde entering the sol-gel reacts with the encapsulated aniline acetate to form the pink coloured complex.

If 7.5 ml of aniline acetate is used instead of 4 ml of aniline acetate then the discs produced are more likely to fragment, more opaque and take longer to dry. If 10 ml of aniline acetate is used then the discs produced are more opaque and very grainy in appearance. If 5 ml of aniline acetate is used the discs produced are occasionally slightly opaque.

To gelate and dry the aniline acetate doped MTMS sol in a shorter period of time, the temperature can be raised. However, if the discs are dried in an oven at temperatures of 60° C. or more for a period of seven days then they are more likely to crack and are less responsive to furfuraldehyde.

Figure 2:
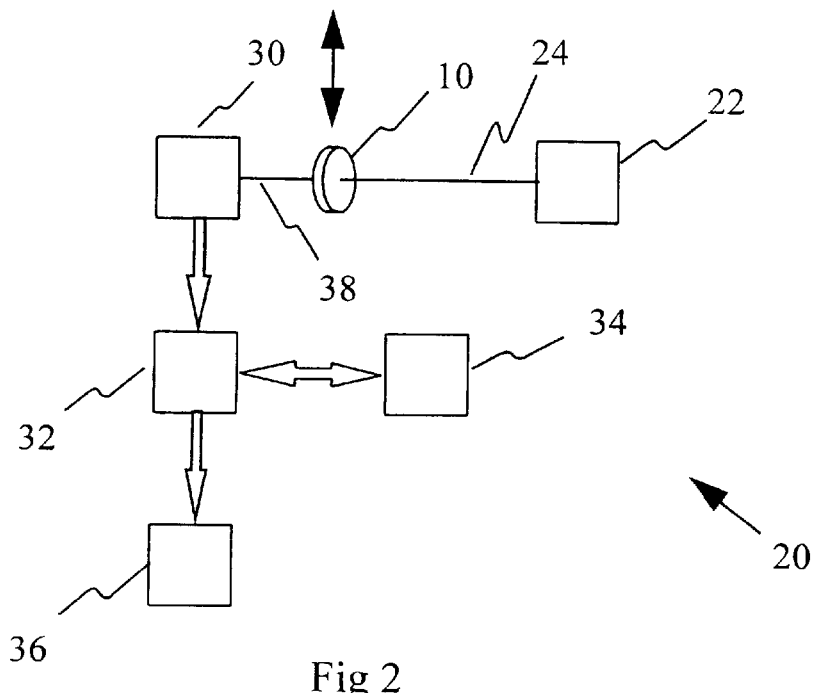
FIG. 2 shows a schematic diagram of apparatus which is used to determine the amount of FFA in transformer oil.

FIG. 2 shows a schematic diagram of testing apparatus 20 which is used to determine the amount of FFA in transformer oil by detecting the colour intensity of the coloured complex. The testing apparatus 20 comprises a light source 22 which produces an input or interrogation signal 24 which is electromagnetic radiation at a wavelength of approximately 530 nm. In this embodiment an LED is used as the light source 22. The reason that light with a wavelength of approximately 530 nm is used is that the absorption of the complex of furfuraldehyde and aniline acetate has an absorption maximum at approximately 530 nm. The input signal 24 (electromagnetic radiation at approximately 530 nm) irradiates and is partly transmitted through a sensor 10 in the light path from the light source 22 to a detector 30. The detector 30 used is sensitive to electromagnetic radiation at 530 nm. The output of the detector 30 is conveyed to a processor 32 which evaluates the output of the detector 30 and compares the evaluated output with reference values stored in a reference 34.

The reference 34 contains a lookup table which is controlled by the processor 32. Each entry of the lookup table has a detected value of light intensity and the corresponding amount of FFA in oil for that value of light intensity. The lookup table information is loaded into the reference 34 prior to using the apparatus 20. The processor compares the detected light intensity with the reference values to determine the amount of FFA in the oil. Once the amount of FFA in the oil is determined, the processor 32 outputs this information to an output display 36.

When transformer oil is to be tested using the testing apparatus 20, prior to inserting the sensor 10 into the oil to be tested, the sensor 10 is inserted into fresh, uncontaminated oil; that is, oil which has never been used and so is free from any FFA. The sensor 10 is then removed from the fresh oil and inserted into the apparatus 20, and the light source 22 is energised. The intensity of light received by the detector 30 when the sensor 10 is inserted, which is the output signal 38 from the sensor 10, is then recorded: this is the control value. The control value is used to scale all of the values of light intensity in the lookup table because the lookup table values of detected light intensity are relative to each other; they are not absolute values.

Once the control value has been determined and the look table values of detected light intensity are appropriately scaled, the sensor 10 is then dipped into the transformer oil under test for a preset period of time (for example 30 minutes) and then removed. The sensor 10 is dipped in the oil for a preset period of time to ensure that the aniline acetate in the sensor 10 has had sufficient time to react with the furfuraldehyde at the relevant oil temperature. The preset period of time required will depend on a number of factors, such as the temperature of the oil.

The sensor 10 is then inserted into the testing apparatus 20 and the sensor is irradiated with the input signal 24. The intensity of the output signal 38 received by the detector 30 is measured and conveyed to the processor 32.

The processor 32 selects the closest value of light intensity in the lookup table to the measured value of the output signal 38 light intensity, and reads the FFA amount entry in the lookup table corresponding to this entry. This corresponding FFA amount is then output to the output display 36. Different types of paper may yield different amounts of FFA upon degradation. Therefore, in determining whether the paper in a transformer has degraded by an unsatisfactory amount, certain characteristics of the transformer (for example the transformer size and the type of paper used) must also be considered in addition to the amount of FFA detected in the transformer oil.

Figure 3A:
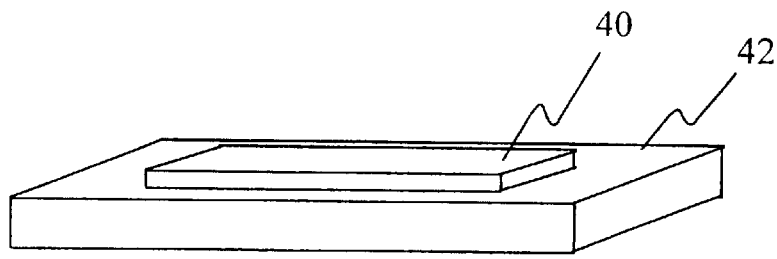
FIG. 3a shows a perspective view of a glass slide coated with a furfuraldehyde sensor in accordance with another embodiment of the invention.
Figure 3B:
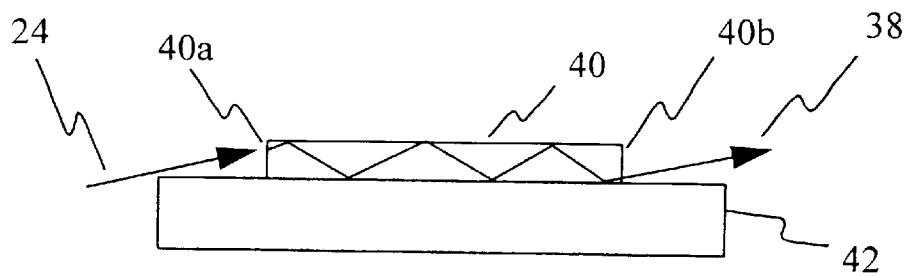

FIGS. 3a and 3b show another embodiment of the furfuraldehyde sensor in which the sensor operates as a waveguide. The sensor is a coating 40 of doped sol-gel material which is applied to a transparent substrate, for example a glass slide 42, where the sol-gel material is doped with aniline acetate. An input signal 24 is applied to one end of the coating (the entrance 40a), the signal 24 passes through the length of the coating 40, reflecting off the sides of the coating 40, and exits at the opposite end of the coating (the exit 40b) as the output signal 38. The output signal 38 is detected and measured using the detection, processing, reference, and output display apparatus described for the apparatus of FIG. 2. The output signal 38 is measured when the substrate 42 and sensor coating 40 is inserted into fresh oil, and also when the substrate 42 and sensor coating 40 is inserted into the oil to be tested. The measurements of the output signal 38 when the sensor coating 40 is inserted into fresh oil and when the sensor coating 40 is inserted into the oil to be tested are used to determine the state of the paper insulation in the same way as described for the apparatus of FIG. 2.

Figure 4:
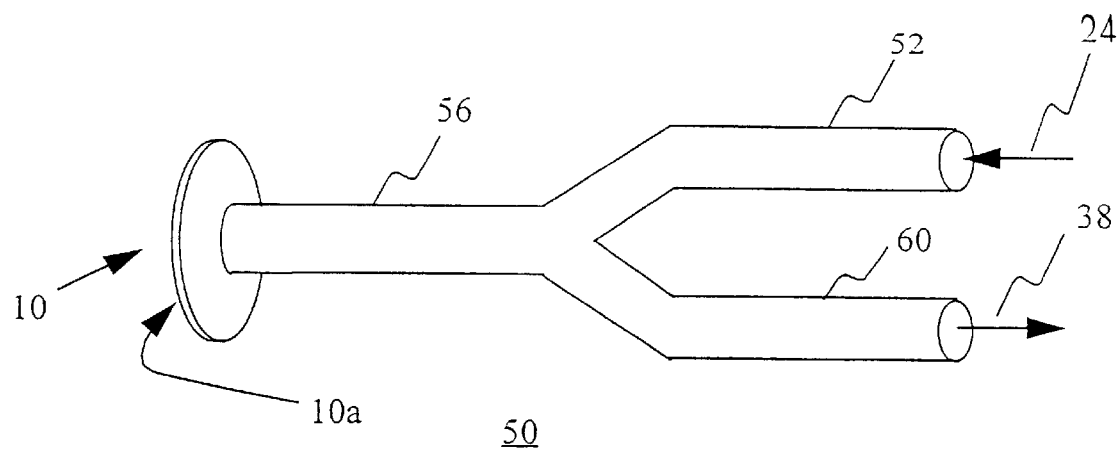
FIG. 4 shows a solid disc-shaped furfuraldehyde sensor in accordance with the embodiment of FIG. 1 connected to a bifurcated fibre optic bundle.

FIG. 4 shows a modified sensor 10 connected to one end of a bifurcated fibre optic bundle 50. The modified sensor has a mirrored rear face 10a, that is, there is a reflective coating applied to the face of the sensor 10 which is not in contact with the bifurcated fibre optic bundle 50. The bifurcated fibre optic bundle 50 has a first arm 52, a common arm 56 and a second arm 60. The bifurcated fibre optic bundle 50 is used in conjunction with the light source 22, detector 30, processor 32, reference 34, and display output 36 as shown in FIG. 2. The light source 22 is connected to the first arm 52 of the bifurcated fibre optic bundle 50 and the detector 30 is connected to the second arm 60 of the bifurcated fibre optic bundle 50. The processor 32, reference 34 and output display 36 are connected to the detector 30 in the same manner as shown in FIG. 2.

Initially, a control value is generated with the modified sensor 10 connected to the fibre optic bundle 50 in an ambient of fresh oil. The control value is used to scale all of the values of light intensity in the lookup table. Once the control value is obtained and the lookup table values have been appropriately scaled, the transformer oil is tested.

To test the transformer oil, the modified sensor 10, which is still connected to the fibre optic bundle 50, is immersed in transformer oil. After a preset period of time (for example 30 minutes) a measurement is taken with the sensor 10 still immersed in the transformer oil. The light source 22 is energised and the input signal 24 propagates along the first arm 52 then along the common arm 56 to the modified sensor 10. The input signal 24 traverses the thickness of the modified sensor 10 before being reflected from the rear face 10a of the modified sensor 10 and again traversing the thickness of the modified sensor 10 before emerging as the output signal 38. The output signal 38 is propagated along the common arm 56 then the second arm 60 of the bifurcated fibre optic bundle 50 into the detector 30. The output signal is used to access the lookup table in the same way as described for the apparatus of FIG. 2.

The relevant FFA amount entry from the lookup table is then output to the output display 36.

This arrangement has the advantage that the modified sensor 10 is fitted to the bifurcated fibre optic bundle 50 prior to immersion into the oil, therefore the test is conducted without having to remove the modified sensor 10 from the oil.

Figure 5A:
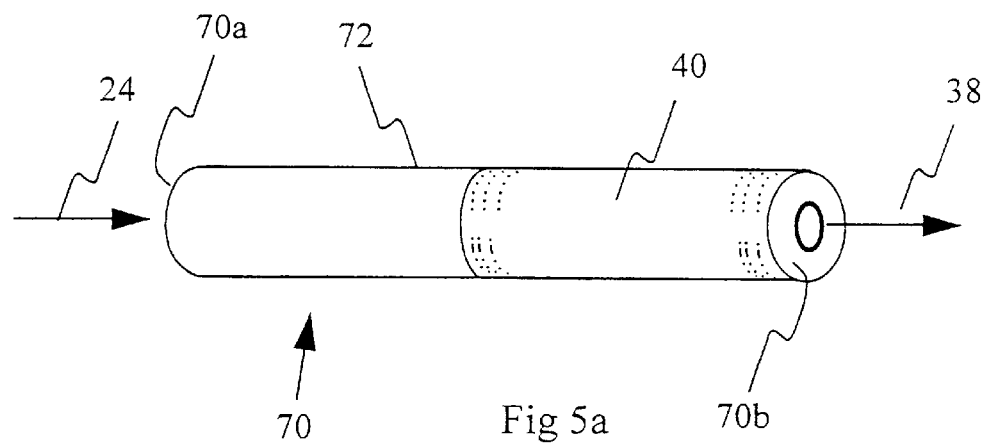
FIG. 5a shows a perspective view of a optical fibre with the usual cladding removed from a localised area of the cable and replaced with a furfuraldehyde sensor.
Figure 5B:
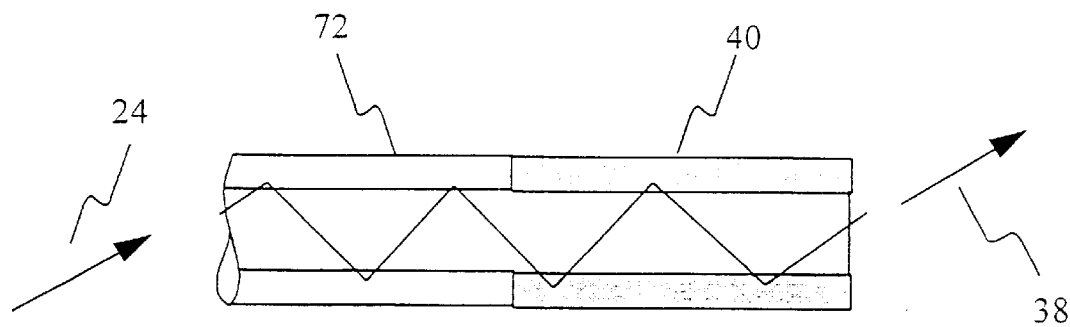

FIGS. 5a and 5b show another embodiment of the furfuraldehyde sensor in which the sensor is part of the cladding of an optical fibre. The optical fibre 70, such as a plastic-clad silica fibre, has its outer cladding 72 completely removed from a portion of its length and replaced with a furfuraldehyde sensor coating 40.

The FFA sensor coating 40 is applied by dipping the fibre 70 into aniline acetate doped MTMS sol. The fibre 70 coated with aniline acetate doped MTMS sold is then left to gelate and dry for a suitable time. Once the sol has gelated and dried the thickness of the coating 40 applied to the fibre optic is measured. If the coating 40 is not thick enough then the procedure is repeated, namely the coated fibre is dipped into aniline acetate doped MTMS sol and allowed to gelate and dry. When the coating 40 has reached the desired thickness, the fibre is ready for use in detecting FFA. The desired thickness may be the thickness that produces the highest absorption (for a given FFA concentration in the oil) of the input signal 24 as it travels along the optical fibre 70.

An input signal 24 is applied to one end (the fibre entrance 70a) of the fibre 70. The intensity of the signal that exits at the opposite end of the fibre (the fibre exit 70b) as the output signal 38 is less than the intensity of the input signal 24 because a portion of the signal was absorbed by the original cladding 72 and by the sensor coating 40. Prior to immersing the coated fibre in transformer oil containing FFA, the sensor coating 40 and the original cladding 72 will not absorb much of the input signal 24. After immersing the coated fibre in transformer oil containing FFA, however, the sensor coating 40 will absorb significantly more of the input signal than the original cladding 72.

The output signal 38 is detected and measured using the detection, processing, reference, and output display apparatus described for the apparatus of FIG. 2. The output signal 38 is measured when the sensor coating 40 on the fibre 70 is inserted into fresh oil, and also when the sensor coating 40 on the fibre 70 is inserted into the oil to be tested. The measurements of the output signal 38 when the sensor coating 40 is inserted into fresh oil and when the sensor coating 40 is inserted into the oil to be tested are used to determine the state of the paper insulation in the same way as described for the apparatus of FIG. 2.

One advantage of having the aniline chemistry immobilised in a sol-gel material is that the colour of the complex produced by the reaction of the aniline acetate with the furfuraldehyde is retained for at least one week; whereas the chemical solutions currently used in industry retain their colour for only a few minutes. The advantages of colour retention are that the test can be repeated a number of times, and the delay between removing the sensor 10 from the oil and performing the test is not critical.

A further advantage of using a sol-gel material is that there is no deterioration of the sol-gel material even if it is left in oil for a period of two months. Thus, the sol-gel material will not introduce chemical substances into the oil if it is left in the oil for slightly longer than is needed to perform the test.

Figure 6:
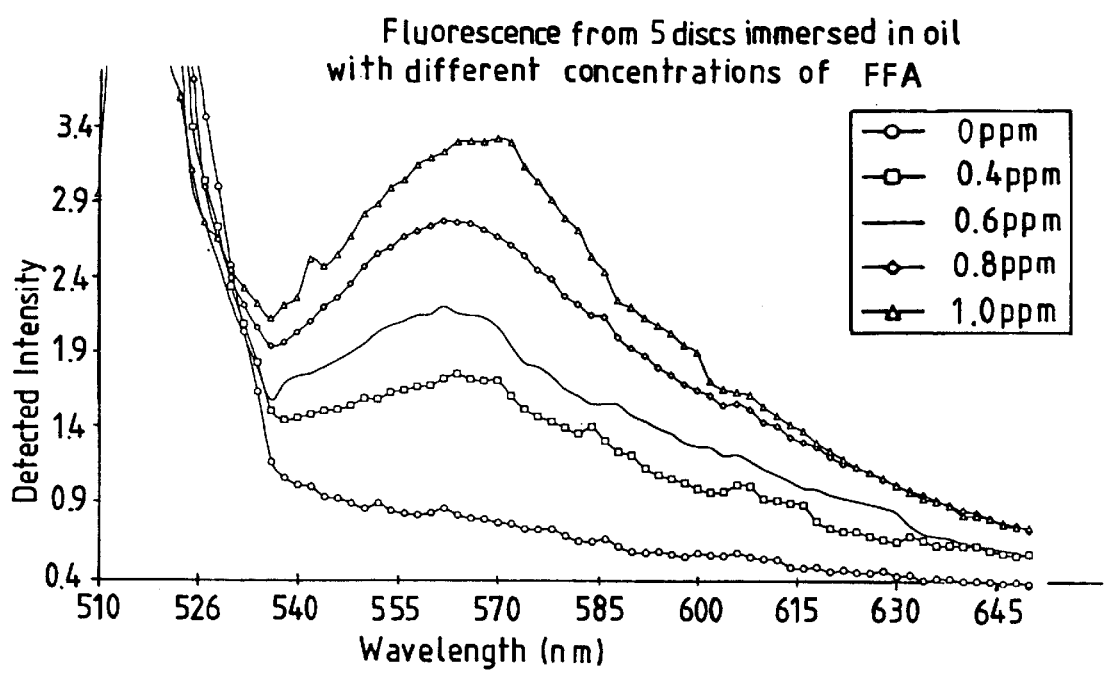
FIG. 6 illustrates fluorescence spectra derived from sensors subjected to different concentrations of furfuraldehyde in oil.

The characteristic of the coloured complex to be measured may be the fluorescence of the complex when irradiated by an optical input signal. This is achieved by irradiating the side of the disc sensor with the input signal preferably having a wavelength of about 525 nm and measuring the resultant wavelength-shifted output signal emitted from the face of the sensor. The output signal, in this case, has a maximum amplitude at about 570 nm and the numeric value of that amplitude correlates with the concentration of FFA in the oil. For example, FIG. 6 shows the resultant fluorescence spectra for sensor discs immersed in oil containing different concentrations of FFA of 1.0 ppm and less. If the zero ppm signal amplitude at 570 nm is taken as a base, the relative magnitudes of the remaining signals show a linear relationship with FFA concentration as shown in FIG. 7.

Figure 7:
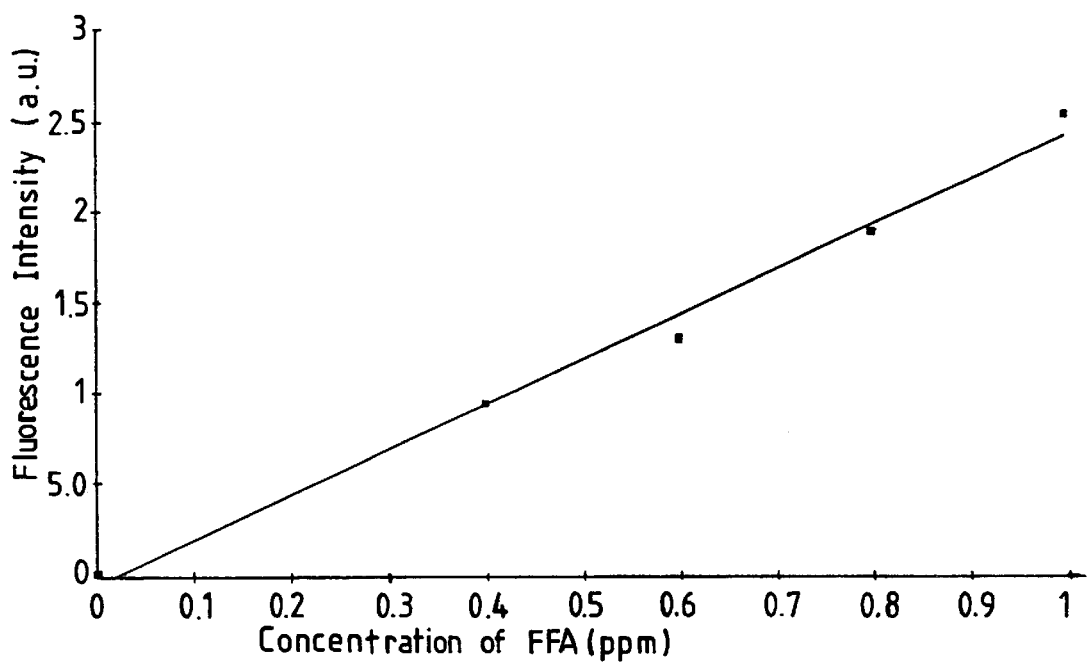
FIG. 7 illustrates the correlation between the furfuraldehyde concentration and the spectra of FIG. 6.

Although FIGS. 6 and 7 illustrate the fluorescent effect between the 525 nm and 570 nm wavelengths, any other set of fluorescent wavelengths may be utilised to provide the required photo-optic measurements. As is well known, fluorescence measurements have a fundamental signal-to-noise advantage over absorption measurements because background radiation at the wavelength of measurement is minimal.

Various modifications may be made to the above described embodiments. For example, the light source may emit light with a fixed wavelength other than 530 nm, but preferably in the range from 500 nm to 600 nm. Similarly, other embodiments may use a light source other than an LED, for example a filament lamp may be used in conjunction with a bandpass filter to provide a light source in the range 500 nm to 600 nm.

In the FIG. 2 embodiment described a single sol-gel disc is used, in other embodiments more than one sol-gel disc (for example eight sol-gel discs, all in the path of the input signal) could be used to increase the colour contrast and hence increase the absorption of the input signal. This has the effect of reducing the intensity of the output signal, thus increasing the difference between the input signal and the output signal.

In the embodiments described hydrochloric acid is used to promote hydrolysis in producing an MTMS sol, in other embodiments other suitable acids, alkalis (for example sodium hydroxide), or catalysts may be used instead.

In the embodiments described a sol-gel is used, in other embodiments other suitable chemical processes may be used to encapsulate aniline acetate in an inert material, providing the material allows ingress of furfuraldehyde. In the embodiments described a circular sol-gel disc is used, in other embodiments a square or rectangular shape of sol-gel material may be used.

In the embodiments described, the 30 minute period for which the sol-gel material is dipped in oil is one suitable time period; however, any convenient period of time may be used provided the sol-gel material has adequate time to form the coloured complex. In other embodiments the transformer oil may be heated (e.g. 90° C. oil) to reduce the time taken for the sol-gel to form the coloured complex. In the embodiment described, an MTMS-based process is used to produce a sol-gel material, in other embodiments a process based on tetraethylorthosilicate (TEOS) may be used. Other suitable quantities of chemicals may be used to produce a sol-gel material.

In the embodiments described a lookup table is used in the reference, in other embodiments the processor may execute an algorithm which uses a polynomial approximation to map the detected light intensity to the corresponding amount of FFA in the transformer oil. In other embodiments of the invention, the control value for the sensor is obtained in an ambient of air rather than the ambient of fresh oil as described in the above embodiments.

In other embodiments of the invention, a coating is applied to the outside of an optical fibre as an area which has a reduced thickness cladding. An input signal is applied to one end of the fibre and an output signal normal to the fibre is detected and measured.

In the embodiment shown in FIGS. 5a and 5b, the entire length of cladding may be removed from the optical fibre and replaced with a sensor coating 40. The optical fibre 70 may be coiled to allow a large amount of fibre to be inserted into a small volume of transformer oil.

In the embodiment shown in FIGS. 5a and 5b, a single fibre 70 is used to obtain a control value of light intensity when the fibre 70 is dipped in fresh oil and then a test value of light intensity when the fibre 70 is dipped in the transformer oil to be tested; an alternative embodiment uses two fibres with identical sensor coatings 40. One of the fibres is inserted into fresh oil and the other fibre is inserted into the transformer oil to be tested. Identical input signals 24 are applied to each fibre and the respective output signals are compared to determine the state of the paper insulation.

Similarly, in the embodiment shown in FIGS. 3a and 3b, a single substrate coated with an FFA sensor is used, an alternative embodiment uses two identical coated substrates. One of the coated substrates is inserted into fresh oil and the other coated substrate is inserted into the transformer oil to be tested. Identical input signals 24 are applied to each coated substrate and the respective output signals are compared to determine the state of the paper insulation.

What is claimed is:

1. A solid sensor for detecting furfuraldehyde in oil, where the sensor comprises a solidified matrix in which aniline acetate is entrapped, and where the matrix is made of an inert material which allows ingress of furfuraldehyde from the oil to react with the aniline acetate to yield an entrapped complex having a characteristic which is photo-optically measurable and which correlates with the concentration of furfuraldehyde in the oil.

2. A solid sensor as claimed in claim 1, wherein the matrix material is a sol-gel.

3. A solid sensor as claimed in either preceding claim and which has sufficient thickness to be self-supporting.

4. A solid sensor as claimed in claim 1 or claim 2 and which comprises a coating carried by a substrate.

5. A method of manufacturing a solid sensor for detecting furfuraldehyde in oil, the method comprising the steps: of forming a colloidal suspension (sol) of methyltrimethoxysilane (MTMS) in a catalyst at an elevated temperature, reducing the temperature of the sol to ambient, preparing liquid aniline acetate, where the reaction temperature is maintained below ambient (20° C.) during the preparation of the liquid aniline acetate, and thereafter stirring into the sol at ambient temperature a quantity of the prepared aniline acetate in liquid form so as to form a sol and aniline acetate mixture, and thereafter gelating and drying the mixture in air substantially at ambient temperature.

6. A method as claimed in claim 5, where the sol is produced at a temperature in the range 75° C. to 90° C. from about 85% by volume MTMS and 15% by volume catalyst in the form of 0.01M hydrochloric acid, and the mixture is formed by adding about 12% by volume of aniline acetate.

7. A method of determining the status of paper insulation in an oil-filled transformer, comprising the steps of: providing a solid sensor formed of a porous solidified inert matrix in which aniline acetate is entrapped, inserting the sensor into the oil for a time sufficient to allow furfuraldehyde to react with aniline acetate encapsulated in the sensor so as to form a complex having a characteristic which is photo-optically measurable and which correlates with the concentration of furfuraldehyde in the oil, thereafter irradiating the sensor with an optical input signal of a fixed wavelength, detecting and measuring an optical output signal received from the sensor, comparing the output signal with a reference to determine the amount of furfuraldehyde that was detected, and providing a qualitative indication of the state of the paper insulation based on the amount of furfuraldehyde that was detected.

8. A method as claimed in claim 7, wherein the optical output signal has the save wavelength as the optical input signal and the measurable difference is due to absorption.

9. A method as claimed in claim 7, wherein the optical output signal has a different wavelength to the optical input signal and the measurable characteristic is due to fluorescence.

10. A method as claimed in claim 8 or 9, wherein the optical input signal has a wavelength in the range 500 nm to 600 nm.

* * * * *